(12) United States Patent
Tam et al.

(10) Patent No.: US 7,167,641 B2
(45) Date of Patent: *Jan. 23, 2007

(54) LOCALIZED SURFACE VOLATILIZATION

(75) Inventors: Kelvin Tam, Hong Kong (HK); Zi Ming Zeng, Shenzhen (CN); William G. Parsons, Racine, WI (US); David P. Mather, Milwaukee, WI (US); Jeffrey L. Harwig, New Berlin, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/984,013

(22) Filed: Nov. 8, 2004

(65) Prior Publication Data

US 2005/0175331 A1  Aug. 11, 2005

Related U.S. Application Data

(63) Continuation-in-part of application No. 10/455,665, filed on Jun. 5, 2003, now Pat. No. 6,909,840.

(60) Provisional application No. 60/386,998, filed on Jun. 6, 2002.

(51) Int. Cl.
*F24F 6/00* (2006.01)

(52) U.S. Cl. ...................................... 392/405; 392/392

(58) Field of Classification Search ........ 392/390–406; 122/366, 367.1, 367.2; 239/44, 45
See application file for complete search history.

(56) References Cited

U.S. PATENT DOCUMENTS

| | | |
|---|---|---|
| 616,049 A | 12/1898 | Archer |
| 2,041,219 A | 5/1936 | Wade |
| 2,140,516 A | 12/1938 | Cowan |
| 2,328,506 A * | 8/1943 | Snelling ...................... 219/200 |
| 2,606,095 A | 8/1952 | Bateman et al. |
| 3,110,256 A | 11/1963 | Barber et al. |
| 3,623,260 A | 11/1971 | Konle |
| 3,778,924 A | 12/1973 | Okui |
| 3,931,492 A | 1/1976 | Takano et al. |
| 3,993,582 A | 11/1976 | Curtis |
| 4,163,038 A | 7/1979 | Nishimura et al. |

(Continued)

FOREIGN PATENT DOCUMENTS

DE    3515460    10/1985

(Continued)

*Primary Examiner*—Sang Y. Paik

(57) ABSTRACT

An apparatus including a replacement refill assembly for dispersing a volatile active into air. The replacement refill assembly includes a reservoir for containing a composition having a volatile active and a wick having an emanating surface from which the active may be volatized. A retainer is included in the apparatus for receiving and retaining the replacement refill assembly. A wire heating element is resiliently supported by opposing spring members so that when the refill assembly is received within the retainer, the spring members bias the heating element against the emanating surface of the wick while yielding an amount sufficient to prevent the heating element from breaking. In one embodiment, the apparatus also includes an air regulator, such as a baffle, for minimizing the flow of air across the heater element. A method and apparatus for controlling the source of power in the apparatus to periodically heat and clean the heating element is further described.

14 Claims, 7 Drawing Sheets

U.S. PATENT DOCUMENTS

| | | |
|---|---|---|
| 4,228,124 A | 10/1980 | Kashihara et al. |
| 4,465,458 A | 8/1984 | Nishino et al. |
| 4,626,666 A * | 12/1986 | Maeda et al. ............... 219/537 |
| 4,693,390 A | 9/1987 | Wilson et al. |
| 4,696,676 A | 9/1987 | Wilson et al. |
| 4,756,118 A | 7/1988 | Evans |
| 4,777,032 A | 10/1988 | Barruet et al. |
| 4,777,345 A | 10/1988 | Manchester |
| 4,780,286 A | 10/1988 | Parent et al. |
| 4,839,144 A | 6/1989 | Martin |
| 4,844,050 A | 7/1989 | Hautmann et al. |
| 4,900,899 A * | 2/1990 | Schreder et al. ....... 219/448.11 |
| 5,094,025 A | 3/1992 | Daniels |
| 5,234,162 A | 8/1993 | Sullivan |
| 5,387,418 A | 2/1995 | Marin et al. |
| 5,458,882 A | 10/1995 | Marin et al. |
| 5,484,086 A | 1/1996 | Pu |
| 5,644,866 A | 7/1997 | Katsuda et al. |
| 5,647,052 A | 7/1997 | Pabel et al. |
| 5,692,095 A | 11/1997 | Young |
| 5,903,710 A | 5/1999 | Wefler et al. |
| 5,945,094 A | 8/1999 | Martin et al. |
| 5,971,367 A | 10/1999 | Skelding |
| 5,976,503 A | 11/1999 | Martin et al. |
| 5,991,507 A | 11/1999 | Benesits |
| 6,104,867 A | 8/2000 | Stathakis et al. |
| 6,123,935 A | 9/2000 | Wefler et al. |
| 6,242,722 B1 | 6/2001 | Provancha et al. |
| 6,248,257 B1 | 6/2001 | Bell et al. |
| 6,278,840 B1 | 8/2001 | Basaganas |
| 6,278,870 B1 | 8/2001 | Millan |
| 6,289,889 B1 | 9/2001 | Bell et al. |
| 6,392,549 B1 | 5/2002 | Wu |
| 6,563,091 B1 * | 5/2003 | Vieira ....................... 219/486 |
| 6,659,301 B1 | 12/2003 | Fellows et al. |
| 6,909,840 B1 * | 6/2005 | Harwig et al. .............. 392/405 |
| 2001/0053283 A1 | 12/2001 | Levine et al. |
| 2002/0005437 A1 | 1/2002 | Ketcha et al. |
| 2003/0189022 A1 | 10/2003 | Fellows et al. |
| 2004/0035409 A1 | 2/2004 | Harwig et al. |

FOREIGN PATENT DOCUMENTS

| | | |
|---|---|---|
| EP | 0470088 | 6/1994 |
| EP | 0362397 | 7/1994 |
| EP | 0911041 | 9/2000 |
| GB | 1123922 | 8/1968 |
| GB | 1123923 | 8/1968 |
| WO | WO 90/133359 | 11/1990 |
| WO | WO 97/28830 | 8/1997 |
| WO | WO 01/93674 | 12/2001 |

* cited by examiner

FIG. 6
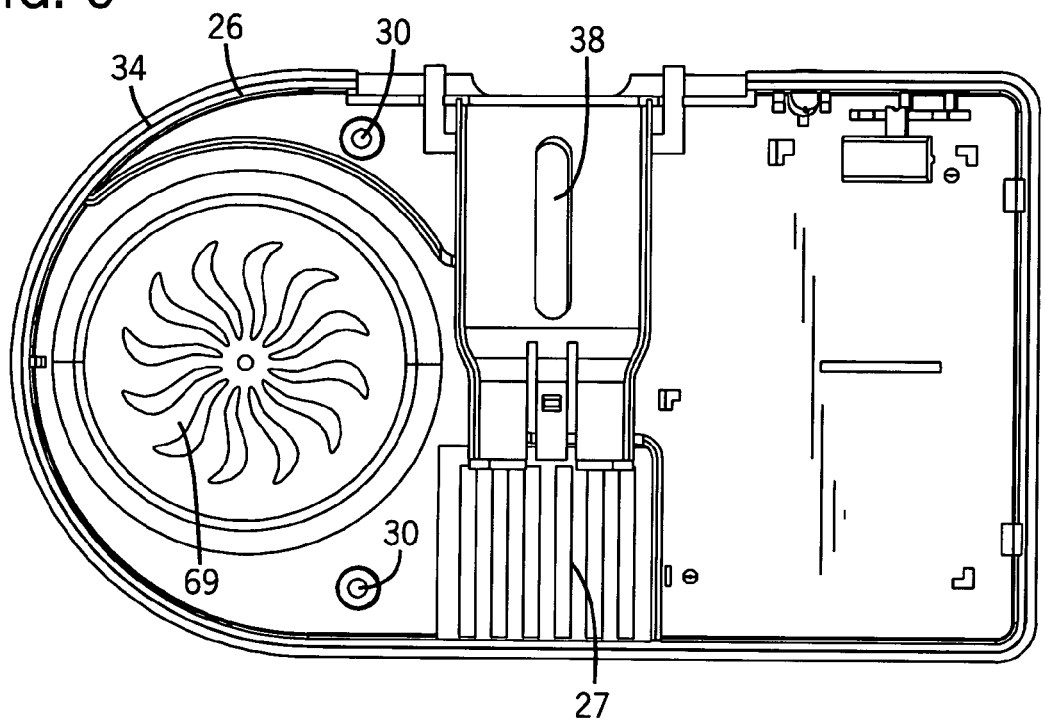
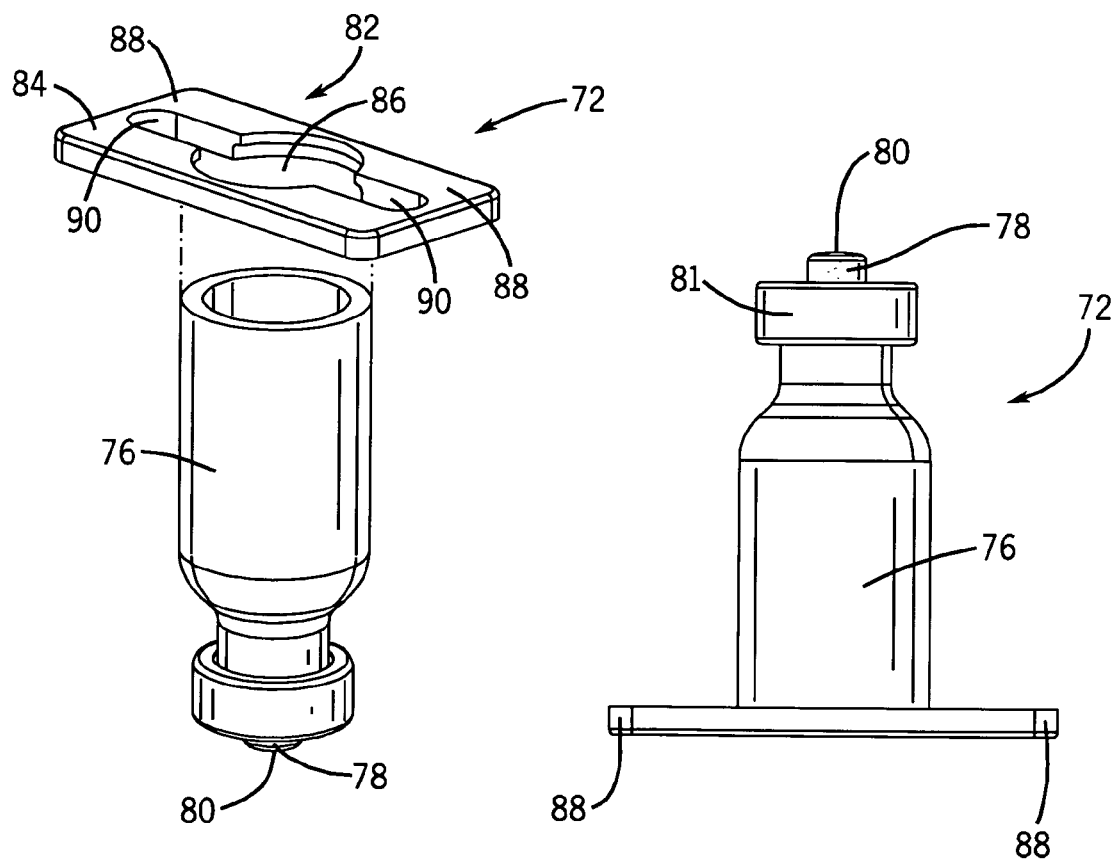
FIG. 7
FIG. 8

LOCALIZED SURFACE VOLATILIZATION

CROSS-REFERENCE TO RELATED APPLICATION

This application is a continuation-in-part of U.S. patent application Ser. No. 10/455,665, filed on Jun. 5, 2003, now U.S. Pat. No. 6,909,840, which claims the benefit of U.S. Provisional Patent Application No. 60/386,998, filed on Jun. 6, 2002.

BACKGROUND OF THE INVENTION

The present invention relates to an apparatus and method for rapid flash-like volatilization of high and low vapor pressure components from liquid or solid emanators, which are in contact with a point or localized heat source. Vaporization is promoted by a geometrically small electrically resistive heater material with variable activation for pulsed or cyclic heating of the emanating surface containing the volatile components.

The field of the invention is primarily directed towards the treatment of air for fragrancing, odor elimination, treatment for insects or pests, air sanitization, air and surface antibacterial or antimicrobial treatment, or other ambient air or surface modification by way of gas or vapor distribution. Applications include devices that are portable (e.g. wearable or carried on an individual's belt), fixed for localized treatment (e.g. covering a relatively small area), or fixed for wider space treatment (e.g. covering an entire room of a house or building). Other fields of use could include commercial and other public environments requiring air or surface modification by gaseous treatment.

Air modification and treatment has been a part of dwelling, recreational, work, and other indoor and localized outdoor environment aesthetics and functionality throughout history. An inherent problem has been that aesthetic or functional volatiles with sufficiently high vapor pressure to adequately treat the environment by unaided means are limited in number and their treatment benefit. As a result there has been a long history of the use of heat to assist in the vaporization of higher molecular weight and lower vapor pressure compounds.

The use of heat increases the range of aesthetic and functional compounds that can be used for air quality management. Some of the first would have used flame (candle systems, stovetops, etc.). Although effective and still in use today, heat from a flame can be difficult to use because the magnitude of heat is difficult to regulate, and a flame typically has wide fluctuations of temperature ranges. Other problems include the affect on larger surfaces, i.e. unintended areas may be raised in temperature, the soot from a flame can blacken components, a flame can give off an unpleasant odor, the solution to be volatized can be rapidly degraded, and there is little adjustment. As a result, many materials are eliminated for use with flame systems.

In addition to flame based systems, there have emerged chemical heat emanation enhancers. Many well-known and simple chemistries are available as described in U.S. Pat. Nos. 6,248,257 and 6,289,889, and include calcium oxides, aluminum copper sulfate, potassium chlorate, calcium sulfate, iron oxide, acids and bases, and others. Chemical heat sources suffer from difficulties in closely controlling temperature and an inability to easily or reversibly stop the reaction.

Another generation of delivery methods includes devices such as compressed gases or aerosols, which propel minute droplets creating great aggregate surface area for volatilization of a liquid composition into the air. These systems work well for instant and situational applications, but present difficulties for continuous air treatment. A simple set of technologies to address this interest area have been dispensing devices with open or semi-closed supported gelatinous, fibrous, or other material of absorbed or adsorbed actives and enhancers that promote passive, unheated emanation by increased surface area. The needed large surfaces cause these products to be of limited use, especially for wearable devices.

Other passive metering systems that have emerged and have been used include semipermeable membranes, wicks, capillaries, porous materials or other fluidic transport and emanating surfaces. Other products such as deodorant and sublimation blocks are also used for dispensing air-treating vapors into the atmosphere by evaporation. The performance of these systems varies widely, and although there are hybrid systems of new materials and designs that promote vaporization by passive methods, they can suffer from the same challenges as do gel and fibrous systems.

There has been increasing use of electrified systems to promote enhanced volatilization, through the use of heat, air movement, electromechanical aerosolizers, or other methods or combinations. Heat and/or airflow have been combined with many of the passive air modification methods mentioned above. The added system energy has sometimes provided more optimal delivery performance. Although these systems can be generally successful, they leave important performance characteristics unaddressed.

SUMMARY OF THE INVENTION

The present invention addresses the above-described needs for improved apparatus and methods using a localized heater with pulsed activation that can be incorporated for use in domestic or commercial, indoor or outdoor, fixed or portable applications.

In one example, an apparatus for dispersing a volatile active into air includes a replaceable refill assembly which includes a reservoir for containing the composition having a volatile active and a wick having an emanating surface. The wick communicates with the composition to deliver the composition to the emanating surface. A retainer is provided on the apparatus for receiving and releasably retaining the replaceable refill assembly. A heating element is resiliently supported by opposing spring members. The apparatus is arranged such that when the refill assembly is received by the retainer, the emanating surface of the wick engages the heating element. When the emanating surface engages the heating element, the spring members that support the heating element bias the heating element with enough force to press the heating element against the emanating surface. In addition, the spring members resiliently yield to prevent the heating element from breaking.

According to this arrangement, an efficient means to facilitate repeated and accurate placement of the emanating surface of the wick against the heating element is provided. In this manner, it is possible to minimize the heating element size, such as for example the diameter of a conventional nickel/chromium/iron alloy resistance heater wire (such as the resistance wire sold by the Driver-Harris Company of Harrison, N.J., under the trademark Nichrome®), which reduces the heat losses due to conduction and minimizes the power necessary to activate the device. The arrangement also advantageously improves the durability of the device by protecting the heating element from breakage.

In addition, in one example of this arrangement, the spring members are composed of stainless steel and include stainless steel connectors for mounting the heater element. Supporting the heating element with a metal of low heat conductivity, such as stainless steel, further reduces heat loss from the heater element and advantageously increases the device's energy efficiency.

In another example, an apparatus (which may be a portable apparatus) for dispersing volatile active into air includes a reservoir for containing a composition having a volatile active, a wick having an emanating surface and communicating with the composition for delivering the composition to the emanating surface. A source of power communicates with a heating element, which is in turn contacts the emanating surface to volatize the active when heated. A housing is provided with at least one air inlet and one air outlet and substantially encloses the reservoir, wick and heating element. A fan is provided in the housing for moving a current of air from the inlet and past the emanating surface to cause egress of the volatile active from the air outlet. Advantageously, an air regulator, such as a baffle, is provided to minimize the flow of air across the heater element. According to this arrangement, the air flow directly across the heating element is reduced, thus lessening heat loss from the heating element and improving the efficiency of the apparatus.

The present application further provides a replaceable refill assembly that is compact, easy to use, and easily aligned and seated in the apparatus. The replacement refill assembly includes a reservoir for containing a composition having a volatile active. A wick is provided that projects from the reservoir and has an emanating surface and which communicates with the composition for delivering the composition to the emanating surface. In addition, a seating flange is provided on the reservoir and assists with alignment and seating of the refill assembly in the apparatus. In one example, the seating flange includes a gripping surface to facilitate manual seating and unseating of the refill assembly to and from the apparatus, respectively. In a further example, the reservoir is longitudinally extended, with the emanating surface being located at one end of the reservoir and the seating flange being located at the opposite end of the reservoir, remote from the emanating surface.

The present invention further provides a method and apparatus for dispersing a volatile active into air, which is self-maintaining and/or self-cleaning. For example, the apparatus includes a reservoir for containing a composition having a volatile active, and a wick communicating with the composition for delivering the composition to an emanating surface. A heating element is placed in contact with the emanating surface. The heating element is in communication with a source of power which heats the heating element to a first temperature to vaporize the volatile active from the emanating surface. A controller is included which controls the source of power to periodically heat the heating element to a second, higher temperature to burn off any residue on the heating element, thus cleaning the heating element.

By the present application, it is recognized that the efficiency and durability of the apparatus and heating methods described above are improved by reducing heat losses due to conduction, radiation, and convection heat transfer, reducing air flow at the heating element, reducing the thermal conductivity of any component touching the heating element, and reducing the overall heating element size.

The present invention also advantageously teaches a refill assembly for repeated replenishing of the composition having the volatile active for dispersion into the atmosphere. The refill assembly includes a reservoir containing the composition having a volatile active, and a wick having an emanating surface for the active. By the present invention, it is further recognized as desirable to improve the usability, functional, and durability characteristics of the refill assembly. For example, it is desirable to provide a replaceable refill assembly that provides an efficient means for registering the refill with the heater such that the wick is consistently placed into contact with the heating element. It is desirable to provide such a refill assembly that prevents turning of the refill assembly as it is registered with the heater, to prevent the wick from abrading the heating element. It is further desirable to provide a refill assembly that is easy to manually grasp and insert into a housing for the heating element.

According to a preferred embodiment of the present invention, a resistance heater wire contacts the wick and is heated to vaporize the active on the surface of the wick into the surrounding air. It has been determined however that repeated use of this arrangement undesirably causes residual build-up of byproducts from the vaporized active to accumulate on the components of the apparatus, including the heater element, such as a resistance heater wire. As such, by the present invention it is recognized as desirable to provide a method and apparatus for automatic cleaning of the heater element, at least at periodic intervals. Such a method and apparatus would improve the efficiency and durability of the apparatus and further eliminates the need to replace the apparatus after repeated uses.

Thus, it is recognized that there is a need in the art for an improved, more efficient and compact volatile dispensing apparatus and a more energy efficient heating method for such an apparatus, together with other features that make the apparatus suitable for use in domestic or commercial, indoor or outdoor, fixed or portable applications.

BRIEF DESCRIPTION OF THE DRAWINGS

Preferred embodiments of the invention are described herein below with reference to the attached drawing figures, wherein:

FIG. 6 is a front view of the inside front cover of the apparatus;

FIG. 7 is an exploded perspective view of a replacement refill assembly for use with the portable apparatus;

FIG. 8 is a front view of the replacement refill assembly in FIG. 7;

DETAILED DESCRIPTION OF THE DRAWINGS

In the examples of the present invention described in detail below, an apparatus for dispersing a volatile active into air is provided. It should be understood that the drawings and specification are to be considered an exemplification of the principles of the invention, which is more particularly defined in the appended claims.

Figure 1:
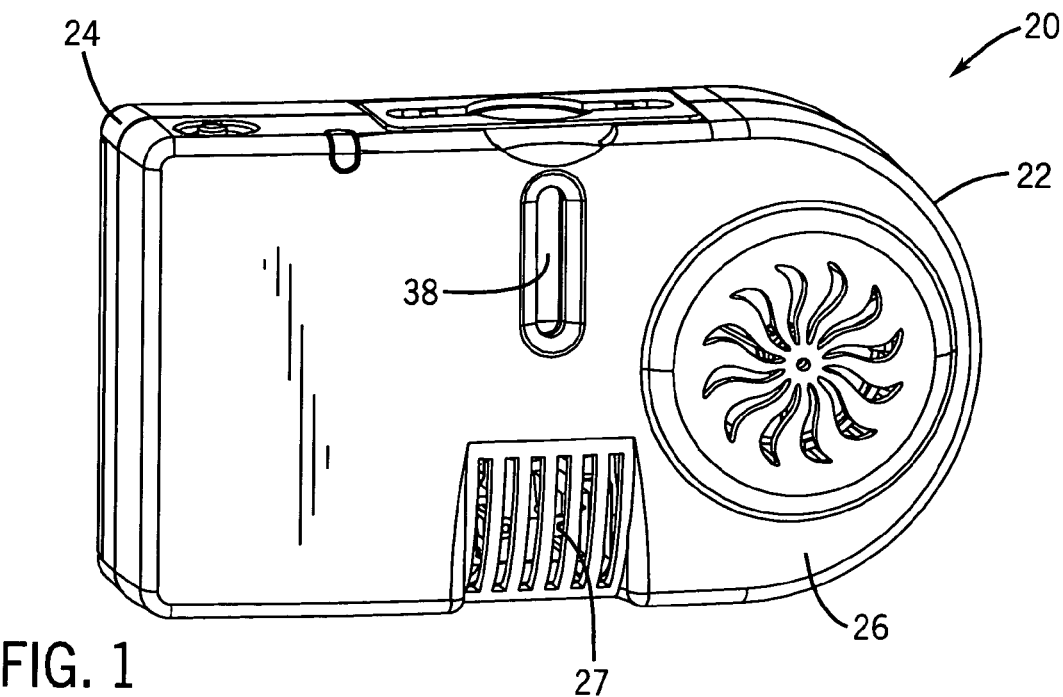
FIG. 1 is a front perspective view of a portable apparatus for dispersing a volatile active into air.

FIG. 1 depicts a portable apparatus (20) for dispersing a volatile active into air. In this example, the portable apparatus consists of a localized and pulsed heater (22) that operates as an integrated system of electrical, mechanical, and fluid systems. The examples described herein were specifically designed for portable and semi-portable fragrancing and insecticide delivery devices. While one aspect of the invention is to provide for a portable fragrancing or insect repellant vapor dispensing device, it should be understood that other vaporizable fluids are contemplated within the scope of the present invention, such as air fresheners, perfumes, deodorants, and the like. Similarly, non-portable dispensing devices utilizing the features of the invention are also possible and contemplated.

Figure 2:
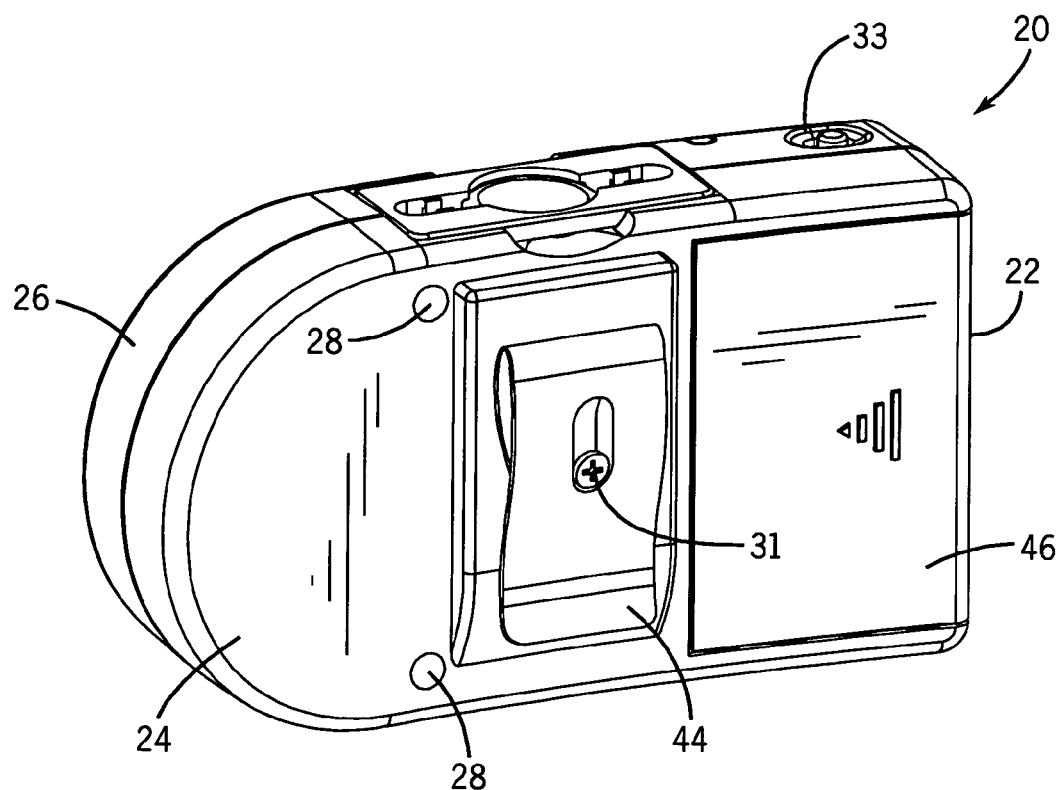
FIG. 2 is a rear perspective view of the apparatus in FIG. 1.
Figure 4:
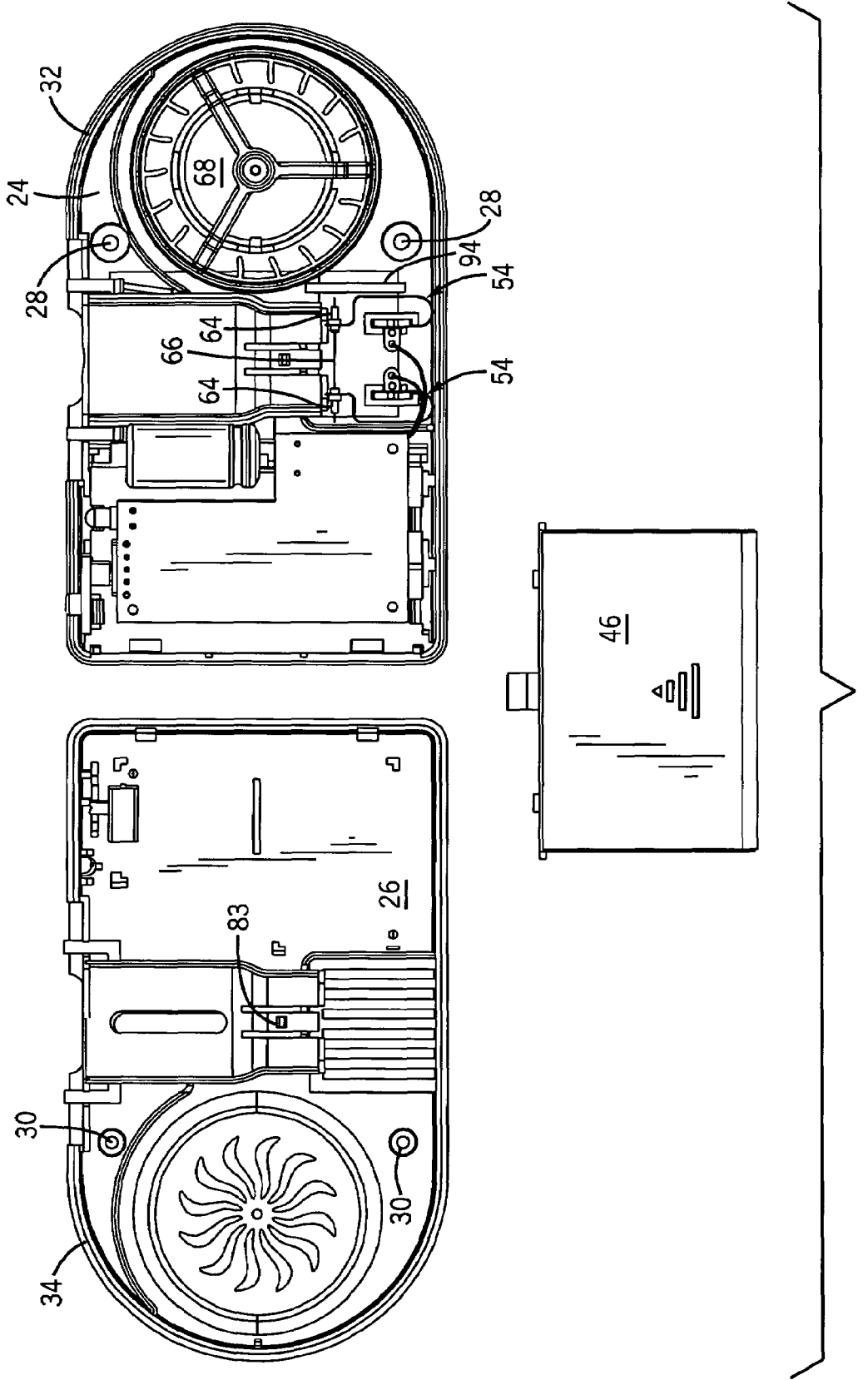
FIG. 4 is a front view of the inside front and rear covers of the apparatus.

Referring now to FIGS. 1 and 2, there is illustrated an example of a portable cyclic localized heater (22) constructed in accordance with the principles of the invention. More specifically, heater (22) includes a housing having a rear cover (24) for supporting the internal components of the heater (22), and a front cover (26) for enclosing those components. Rear cover (24) includes a pair of screw holes (28) for receiving screws to secure the rear cover (24) to the front cover (26). Screws are received by the front cover (26) in corresponding screw holes (30), shown in FIG. 4. Rear cover (24) is in the shape of a shallow tray and includes a lip (32) at its peripheral edge which engages a corresponding lip (34) on the front cover (26) so that rear cover (24) may be joined with front cover (26). Front cover (26) is thus removable so as to permit access to the interior of heater (22), if desired, as shown in FIG. 4.

Rear cover (24) and front cover (26) may be made of any suitable, lightweight material such as a wide variety of commercially available plastics that are produced by conventional processes and known to those skilled in the art. Any plastic housing material that is selected, however, must be compatible with the particular active volatile fluid that is to be vaporized. Typically, rear cover (24) and front cover (26) may be made of a commercially available polycarbonate material manufactured by known injection molding methods. Rear cover (24) and front cover (26) can be of any suitable dimension such that it may be readily portable whenever desired.

As shown in FIG. 1, front cover (26) further includes a window (38) for viewing the amount of volatile active present in the apparatus (20). As will be discussed further below, the window (38) allows a user to identify when the replacement refill (72) that is seated in the heater (22) (shown in FIGS. 7–11) needs to be replaced. Front cover (26) also includes a vent (27) for allowing air carrying volatilized active to escape the heater (22), and be directed downwardly out of the housing, as will be discussed further below with reference to FIG. 12.

As shown in FIG. 2, the rear cover (24) includes a clip (44) for attaching the portable apparatus (20) to the clothing or other items of a user. The clip (44) may be made of any material suitable for supporting the weight of the heater (22) and may be permanently of removably attached to the heater (22). In the embodiment shown the clip is removably attached by screw (31). Rear cover (24) also includes a removable lid (46) which allows access to replaceable batteries (47) contained within the portable apparatus (20). In the embodiment shown, the portable apparatus (20) is powered by two alkaline batteries (47) (shown in FIG. 11). However it will be recognized by those skilled in the art that a wide variety of suitable power sources may be employed to obtain the objects of the present invention. For example, more or fewer batteries may be used, and batteries (47) may be of the rechargeable type. Power may also or alternately be provided by a permanent power source.

Figure 3:
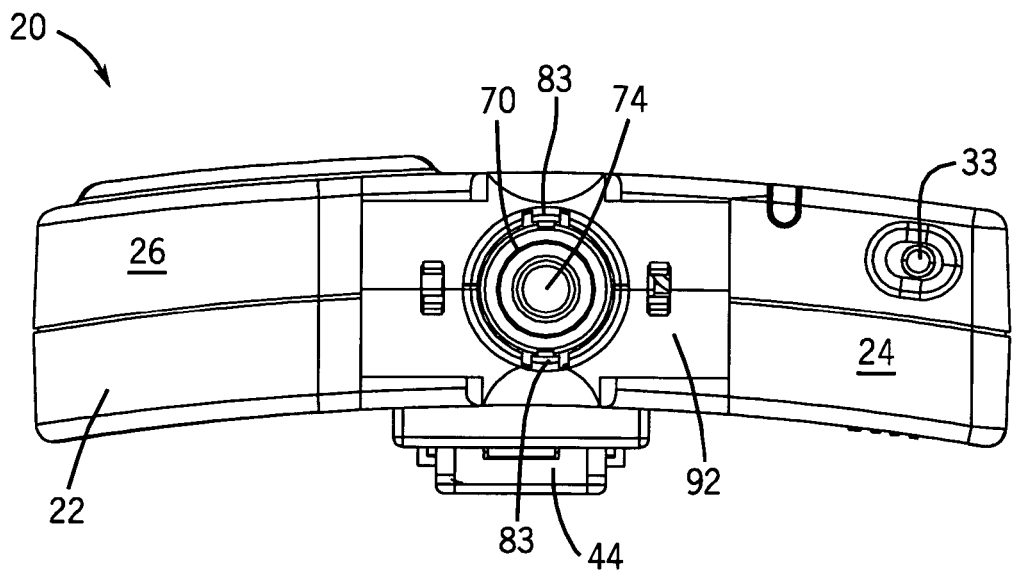
FIG. 3 is a top view of the apparatus in FIG. 1.

As shown in FIG. 3, an on/off switch (33) is also provided on the top of the front cover (26). The on/off switch communicates with the control circuitry within the heater (22) to allows for manual activation and deactivation of the heater (22). As also shown in FIG. 3, the inside front cover (26) and inside rear cover (24) define a retainer portion (70) for receiving a replacement refill (72), shown in FIGS. 7 and 8. In the embodiment shown, the retainer portion (70) includes a plastic cup that is sized slightly larger than the replacement refill (72). The retainer portion (70) is divided in two parts, with one part each being held by the front cover (26) and rear cover (24), respectively. As such, when the front cover (26) and rear cover (24) are assembled together, the retainer portion (70) forms a space for receiving the replacement refill (72), the space being slightly larger than the replacement refill (72). In addition, the retainer portion includes an aperture (74) at its lower end for receiving the wick (78) of the replacement refill (72), as will be discussed further below. The front cover (26) and rear cover (24) also define a seating recess (92) for receiving a seating flange (82) on the replacement refill (72). This seating arrangement will also be discussed further below.

Figure 5:
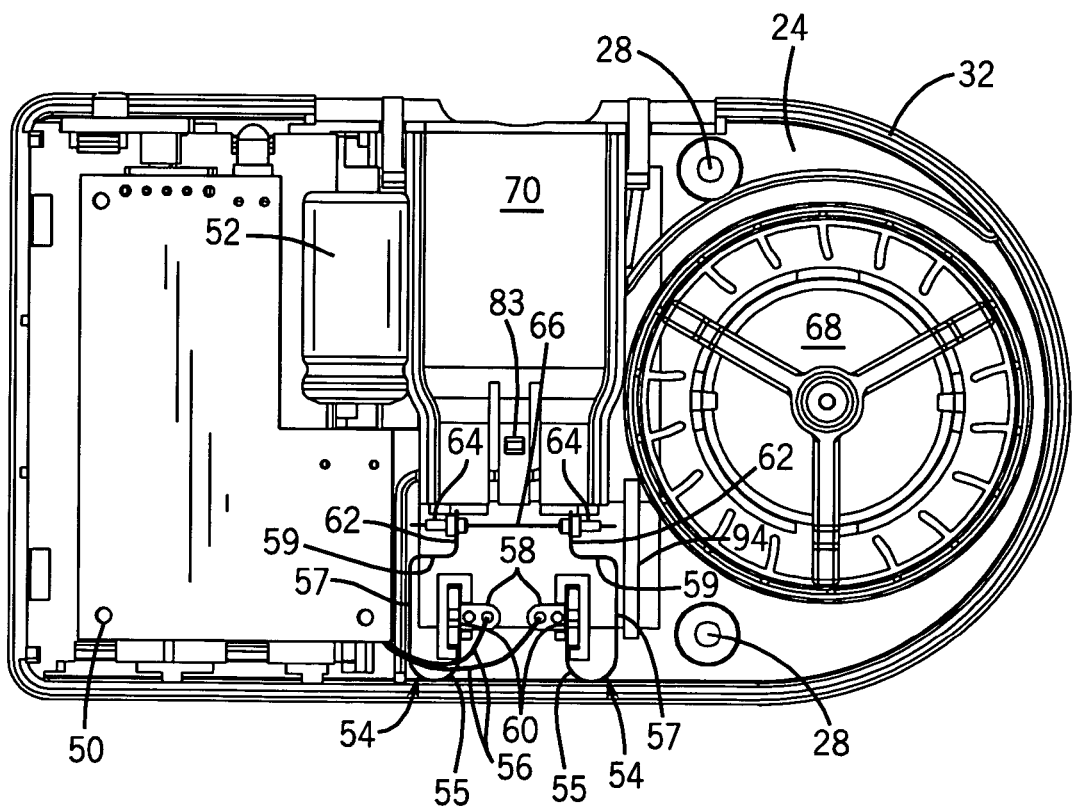
FIG. 5 is a front view of the inside rear cover of the apparatus.

Referring now to FIGS. 4 and 5, the inside rear cover (24) includes a fan (68) for directing air through the apparatus (20). In addition, the inside rear cover (24) contains solid state electronic circuitry such as a circuit board (50) and a capacitor (52). The pulsed electrical cycling of heater (22) is achieved by the solid state electronic circuitry, but is not limited to the specific circuitry illustrated. The primary function for the electronics is to switch the heater (22), including fan (68), on and off at predetermined intervals. The on/off duty cycle reduces the energy used and increases battery life as compared with a device that runs continuously. The heater control timing can be set to operate for a predetermined, overall time duration, e.g., two hours, four hours, eight hours, etc. or can be set to turn the heater (22) on and off for predetermined time periods, e.g., on for five seconds and then off for five seconds, for as long as the low voltage detector indicates a good battery. The duty cycle may be adjustable by changing a resistor on the printed circuit board.

The electronic circuitry is placed in electric communication with a spring assembly comprised of a pair of spaced and opposing substantially C-shaped spring members (54) that resiliently support a heating element (66). To conserve energy loss, the spring members (54) preferably consist of a metal of low conductivity, such as stainless steel, and are in the form of leaf springs each having a lower fixed end (60) and an upper free end (62). A pair of electrical wires (56) extend from the circuit board (5) and are connected to electric mounting plates (58). The mounting plates (58) are, for example, welded or spot welded to the electrical wires (56). The fixed end portions (60) of each of the two opposing springs (54) are also spot welded to its respective mounting plate (58) to place the springs (54) in communication with the electrical wires (56) and the electronic circuitry. In the embodiment shown, the springs (54) are identical in configuration and each has a bottom unshaped curved portion (55) which transitions about 180° from its fixed end portion (60) into a longitudinal linear portion (57). Linear portion (57) in turn transitions about 90° into a lateral portion (59), which in turn transitions about 90° upwardly into the free end portion (62). The free end portions (62) of the springs (54) are welded or spot welded to connectors (64), which in turn mount the heating element (66) therebetween. Preferably, connectors (64) are also constructed of stainless steel to further reduce energy loss. Although the particular embodiment shown is preferred, it will be recognized by those skilled in the art that numerous spring arrangements are feasible and would accomplish the objectives of the present invention. Any spring assembly that functions to resiliently support the heating element (66) so that when the refill assembly (72) is inserted into retainer (70) the spring assembly bias the heating element (66) against the emanating surface (80) of wick (78) and resiliently yields to prevent the heating element (66) from breaking may be used.

In the embodiment shown, the heating element (66) is a resistance heater wire. Important to the selection of the resistive heating element is its effectiveness at volatilizing solutions and its energy efficiency. The gauge of the wire is preferably selected to have higher resistance and less energy draw to generate needed wire temperatures. Like other resistive materials, there is an issue of thinning wire diameter and the propensity for failure. Fine, large gauge heater wires are relatively fragile and are subject to mechanical failure during manufacturing, transportation, consumer handling and use. In addition, thermal cycling induces stresses and fatigue in the heating elements, which may result in heater failure. Undesirable oxidation of the heater material can also occur causing weakening and possible failure. Thus, one of the primary advantages of the spring assembly of the present invention is its ability to resiliently support the wire heating element (66) so that when the refill assembly (72) is inserted, spring members (54) not only bias heating element (66) against the emanating surface (80) of wick (78) but also resiliently yield to prevent breaking heating element (66).

As shown in FIG. 6, the rear cover (26) includes an inlet vent (69) for drawing air in to the apparatus 20 via fan (68), an outlet vent (27) for allowing egress of air from the heater (22), and a window (38) for viewing the level of active in the replacement refill (72) when it is inserted in the heater (22).

Referring now to FIG. 7, one example of a replacement refill (72) is shown. The replacement refill (72) is removable from the apparatus (20), allowing for replacement of the refill (72) after desired vaporization of the fluid contained therein. This allows for the interchanging of a variety of like-dimensioned refills (72) containing a wide variety of vaporizable liquid substances. The replacement refill (72) includes a reservoir (76) arranged to contain a volatile solution or fluid, such as an evaporable liquid insecticide or an evaporable liquid insect repellant, fragrance or the like. The reservoir (76) can be constructed as to be disposable and replaceable by new reservoirs containing a fresh supply of active. Also, preferably, the reservoir (76) is at least semi-transparent in order to provide a user with the visual ability to determine the amount of vaporizable active or liquid remaining in the apparatus (20). Further, although the preferred composition is one that contains the active ingredient in a liquid solution, the composition may also be a solid, semi-solid or gel formulation under ambient conditions. In each case, the composition includes the active ingredient and a carrier for the active ingredient. The carrier may include one or more blowing agents, solvents, stabilizers, synergists, dyes and perfumes.

The replaceable refill (72) further includes a projecting wick (78) which has a first end received within the reservoir (76) and a second end extending out of the reservoir (76) and having a relatively flat tip or emanating surface (80). In use, capillary action draws active through the wick (78) and introduces the active to the emanating surface (80) at the flat tip of the wick (78). The wick (78) may be constructed from natural materials, fibers, non-woven, sintered polymers, ceramics, metal foams, open capillary tubes of ceramic, glass, or other material. A critical consideration for selection of any of these materials is the temperature required for surface heating for the affluent being volatized. The preferred wicking material is ceramic, in part because of its high temperature tolerance. It shares other features with some other wicks with the ability to tailor for size to address wicking rates and fouling, it has insulative properties to further minimize heat transfer, and is readily available as a material. If the wick substrate is conductive, then a dielectric material layer of a few thousandths of an inch in thickness must be placed between the electrically resistive heater and the substrate. Materials not requiring the need for dielectrics are preferred for their reduced cost, retained capillary pores for wicking, thermostability, etc. Ceramic wicks are also preferable in that they can withstand heater deposition processing temperatures, if required. Other wick materials include wicks made from sawdust and silica/sand mixtures that are able to withstand needed temperatures to volatilize the actives.

As shown in FIGS. 7 and 8, the replaceable refill assembly (72) advantageously includes a seating flange (82), which in the example shown includes a plate member (84) that is attachable to the reservoir (76) of the replacement refill (72). The seating flange (82) may be permanently affixed to the refill (72), or alternately may be releasably received by the refill (72), such as in a snap-fit arrangement. In the embodiment shown, the seating flange (82) includes an aperture (86) sized slightly larger than the outer circumference of the reservoir (76) for receiving the reservoir (76) in a snap-fit arrangement. As shown in FIGS. 7 and 8, the seating flange (82) has a pair of opposing wings (88), each having an aperture (90) formed therethrough. Advantages provided by the seating flange (82) are that it provides the user with the ability to easily and accurately seat and unseat the refill (72) in recess (92) of heater (22) without causing damage to the refill assembly or the various components of the heater (22). The seating flange (82) may be formed metal or plastic, or a wide variety of materials suitable for achieving the above advantages.

The refill assembly (72) also includes a collar (81) disposed adjacent wick (78) opposite flange (82). Collar (81) engages a plurality of circumferentially spaced resilient latches (83) formed at the lower end of retainer (70) to provide a snap-fit arrangement to retain refill assembly (72) in retainer (70).

Latches (83) thus provide sufficient force on collar (81) to hold refill assembly (72) within retainer (70), yet enables refill assembly (72) to be readily removed and replaced when necessary.

Figure 9:
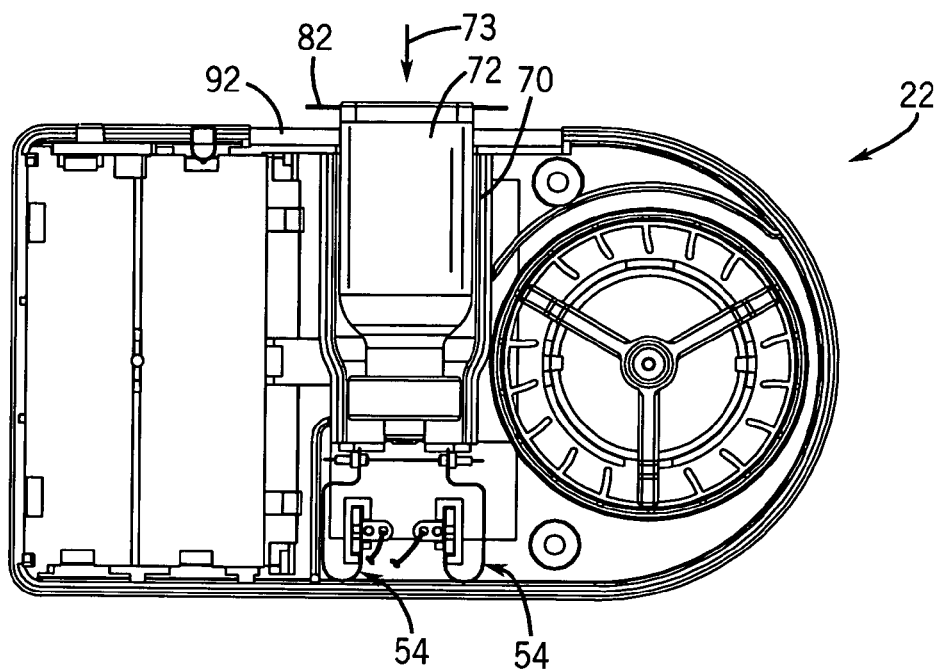
FIG. 9 is a front view of the inside rear cover of the apparatus with replacement refill assembly being inserted.
Figure 10:
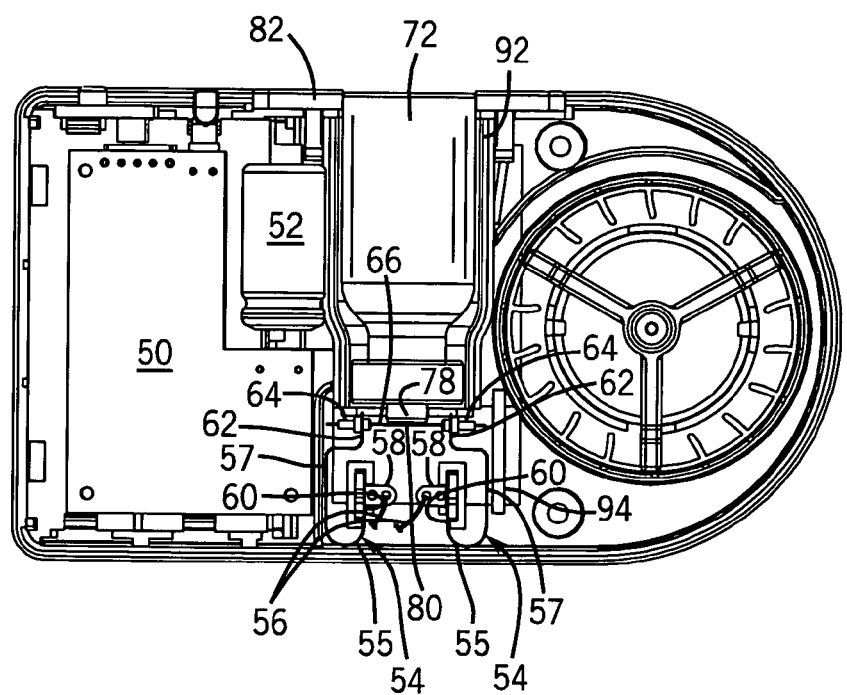
FIG. 10 is a front view of the inside rear cover of the portable apparatus with replacement refill assembly inserted.
Figure 11:
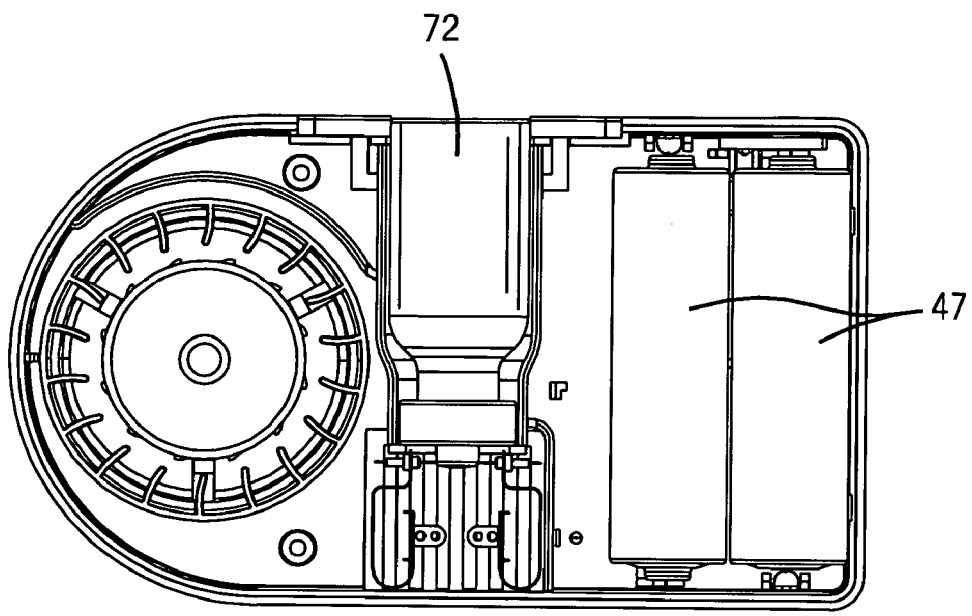
FIG. 11 is a front view of the inside front cover of the portable apparatus with refill assembly inserted.

Referring to FIGS. 9 and 10, in use, the replacement refill assembly (72) is manually inserted into the retainer portion (70) of the heater (22) in the direction of arrow (73) until the seating flange (82) seats within the recess (92). The recess (92) most clearly shown in FIG. 3, is sized slightly larger than the seating flange (82) and thus receives the seating flange (82) in a snap fit engagement. Because the recess (92)

and seating flange (82) are rigid and can only engage each other in a certain alignment, the recess (92) and seating flange (82) ensure that the refill (72) is properly inserted into and aligned with the heater (22), and ensure that components of the refill (72) and heater (22) are not damaged during removal and replacement of the refill (72).

FIG. 10 illustrates the replacement refill (72) properly aligned with and inserted into the retainer portion (70), and the wick (78) inserted into the aperture (74) in the retainer portion (70). In addition, the emanating surface (80) of the wick (78) is accurately placed into contact with the heating element (66), which in the example shown, is a resistance heater wire (66).

It is to be noted that the force of the wick (78) against the resistance heater wire (66) during installation of the replacement refill (72) must be controlled. If there is too little contact force between the wick (78) and the heater element (66) sufficient contact is not provided to cause volatilization at the emanating surface (80). If there is too large a force, the wick (78) may break the resistance heater wire. In addition, if the refill assembly is rotated during installation, the wick (78) will abrade the heater element (66) undesirably wearing down and/or eventually breaking the heater element (66).

Advantageously, breakage of the heater element is prevented by the stainless steel spring support assembly of the present invention. According to the present invention, as the refill assembly (72) is inserted into the retainer portion (70), wick (78) presses down onto and engages the resistance heater wire (66). The stainless steel springs (54) flex to bias the resistance heater wire (66) with sufficient force against the emanating surface (80) to allow for volatilization to occur. However the stainless steel springs (54) are also gauged to yield an amount sufficient to prevent the resistance heater wire (66) from breaking under the pressure from the wick (78). The unique seating flange arrangement on the replaceable refill assembly encourages the user to insert the refill (72) directly into the retainer portion (70), without turning. As those skilled in the art will recognize, this arrangement provides the much needed ability to replace exhausted refill assemblies (72) numerous times, without incurring breakage to the heating element (66). In addition, the combination of the springs (60, 62) and the seating flange (82) on the replaceable refill (72) encourage proper seating of the replacement refill (72) in the retainer portion (70) without causing breakage to the replacement refill (72) or the resistance heater wire (66).

Referring now to FIG. 10, once the replacement refill (72) is fully seated in the apparatus (20), the emanating surface (80) is placed in direct contact with the resistance heater wire (66). As active is drawn by capillary action through the wick (78) to the emanating surface (80) the active is also placed in direct contact with the heating element (66).

Figure 12:
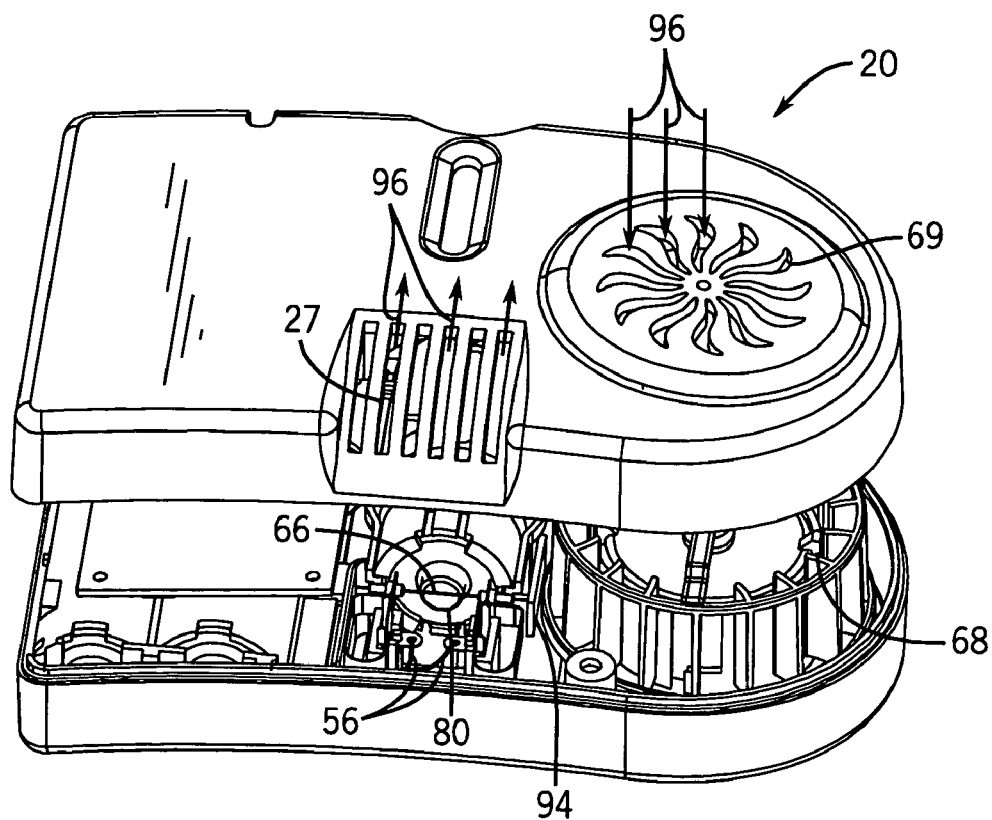
FIG. 12 is an exploded view of the portable apparatus showing air flow therethrough.

Referring to FIG. 12, in use, the control circuitry supplies electricity to the stainless steel springs (54) via the electrical wires (56). The electricity is fed via the stainless steel connectors (64) to the resistance heater wire (66). The resistance heater wire thus heats the emanating surface (80) and thus volatilizes the active. Simultaneously, the control circuitry activates fan (68), which draws air in through inlet vent (69). To conserve energy, it is desirable to minimize the air flow in contact with the heater element (66). This is because the moving air cools the heater element, and as a result more power must be supplied to the heater element to maintain a desired temperature which in turn reduces battery life. However, one also would benefit from evacuating the air inside the housing rapidly, to reduce the active concentration surrounding the heating element (66) because a lower concentration allows for easier volatilization. Therefore, it is desirable to move air inside the housing, but also to utilize an air regulator to prevent flow across the heater element. FIG. 12 illustrates a method of accomplishing this goal when used in combination with a fan. More specifically, baffle (94) is provided as the air regulator. Baffle (94) is disposed between the fan (68) and the heating element (66) in the path of the air currents (96) created by the fan (68) to prevent direct contact of the air currents (96) with the heating element (66).

As shown in FIG. 12, the air is drawn in through the inlet vent 69, across the baffle (94), adjacent the heating element (66) and out of the outlet vent (27). Outlet (27) has a configuration that directs air flow downwardly out of the housing, as seen best in FIG. 1.

In preferred embodiments of the present invention, a volatilizable liquid containing the active ingredient ETOC is utilized. ETOC can be volatilized at a reasonably low temperature, providing an energy efficient device and process. However, during the volatization process, byproducts and/or impurities can often accumulate or polymerize as a coating on the heating element. As this coating builds, it increasingly reduces the effective active delivery from the device.

According to the present invention, the electronic circuitry periodically delivers a brief, extra current flow to the heating element. The extra current briefly heats the heating element sufficiently to burn off any coating or byproducts thereon when a material such as commercial preparations of ETOC is used as the material to be volatilized. When ETOC is used, for example, preferably the heating element is heated every 30 minutes to a temperature of about 185° C. This occasional pulsing arrangement thus allows use of low temperature normal delivery mode combined with a method of "self-clearing" the coating.

Figure 13:
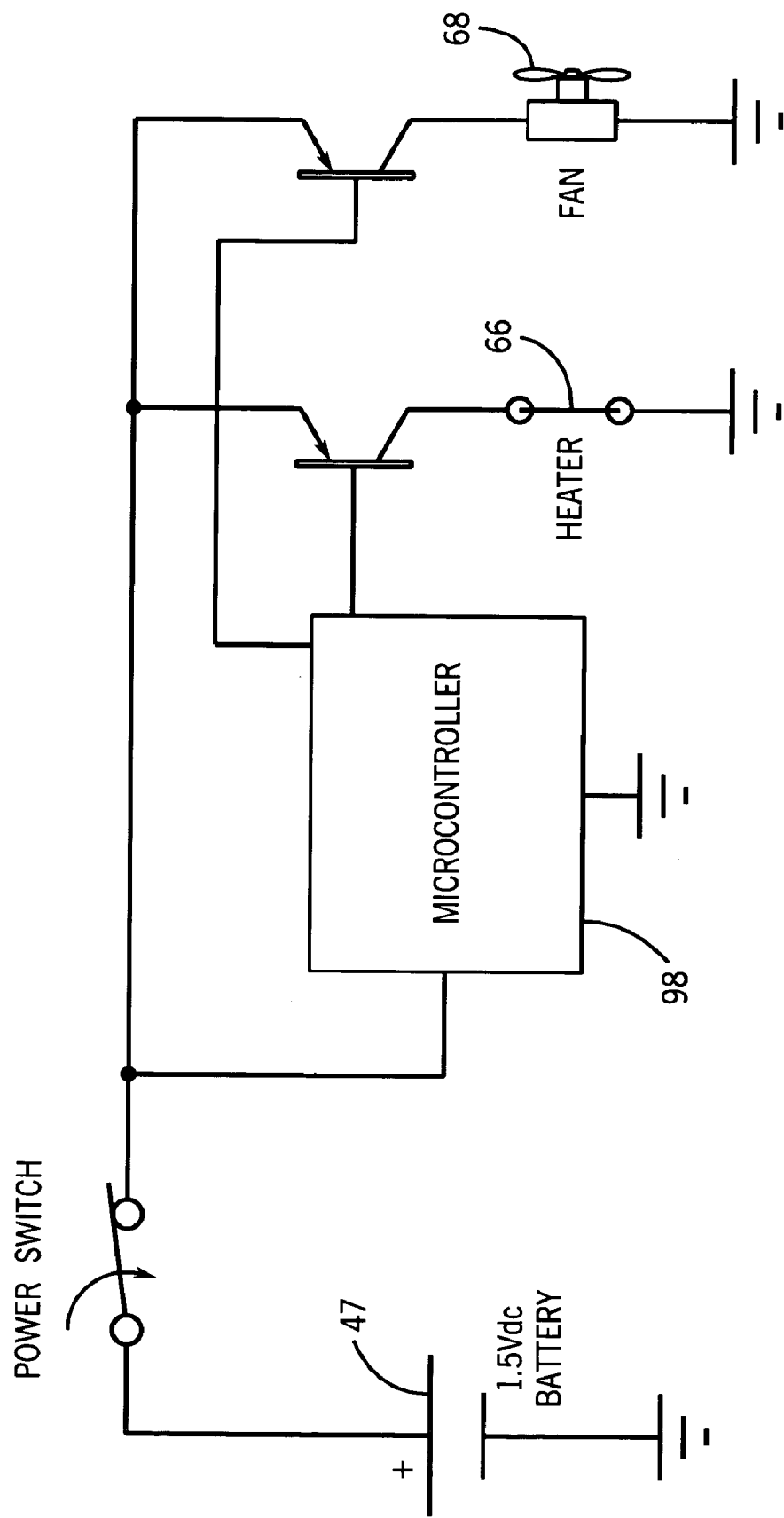
FIG. 13 is a schematic circuit diagram illustrating one example of electronic circuitry for controlling the apparatus of FIG. 1.

FIG. 13 illustrates one example of a circuit for providing this self-cleaning feature. A microprocessor (98) can be programmed to operate either the fan (68) or the heater (66) on, for example, a "5 sec. on/5 sec. off" basis, to limit battery use. The particular time intervals can be modified, although the 5 second periods are currently preferred. The microprocessor (98) can also be programmed to deliver current sufficient to heat the wire (66) to an elevated level, doing so at whatever interval is determined to be useful to keep the wire clear of accumulated material.

While this invention is susceptible to embodiments in many different forms, the drawings and specification describe in detail a preferred embodiment of the invention. They are not intended to limit the broad aspects of the invention to the embodiment illustrated.

The invention claimed is:

1. An apparatus for dispersing a volatile active into air, the apparatus comprising:
   a replaceable refill assembly comprising a reservoir for containing a composition having a volatile active and a wick having an emanating surface and communicating with said composition for delivering said composition to said emanating surface;
   a retainer for receiving and releasably retaining said replaceable refill assembly;
   a heating element engageable with the emanating surface of said wick;
   a spring assembly resiliently supporting and directly attached to opposite ends of said heating element so that when said refill assembly is received by said retainer said spring assembly biases said heating element against said emanating surface and resiliently yields to prevent said heating element from breaking, and a seating flange attached to said reservoir and snap-fit into a recess aligned with said retainer such that said refill assembly is non-rotatably received in said retainer, the combination of said spring assembly and said seating flange enabling proper seating of said refill assembly in said retainer without causing breakage to said refill assembly and said heating element.

2. The apparatus of claim 1, wherein said spring assembly comprises a pair of opposing substantially C-shaped spring members, each having a free end and a fixed end, and said heating element comprises a wire extending between said free ends so that the free ends of said spring members move toward each other when said emanating surface engages said heating element.

3. The apparatus of claim 2, wherein said spring members comprise stainless steel.

4. The apparatus of claim 1, wherein said wire heating element comprises a combination nickel, chromium and iron alloy resistance heater wire.

5. The apparatus of claim 2, further including a pair of connectors for releasably mounting opposite ends of the wire heating element to the free ends of said spring members.

6. The apparatus of claim 1, wherein said spring members comprise a pair of leaf springs.

7. An apparatus for dispersing a volatile into the air, the apparatus comprising:
a reservoir for containing a composition having a volatile active;
a wick having an emanating surface and communicating with said composition for delivering said composition to said emanating surface;
a heating element in contact with said emanating surface;
a source of power communicating with said heating element to heat said heating element and vaporize said volatile active;
a housing substantially enclosing said reservoir, wick and heating element, said housing comprising at least one air inlet and one air outlet;
a seating flange attached to said reservoir and snap fit into a recess formed on said housing such that said reservoir is non-rotatably received on said housing, said seating flange enabling proper seating of said reservoir in said housing without causing breakage to said reservoir and said heating element;
a fan for moving a current of air from said inlet through said housing to cause egress of said volatile active from said air outlet; and
an air regulator disposed within said housing to prevent said air current from flowing directly across said heater element.

8. The apparatus of claim 7, wherein said air regulator comprises a baffle disposed between said fan and said heater element to prevent direct contact of said air current with said heating element.

9. The apparatus of claim 7, wherein said air regulator defines a passageway formed adjacent to said heater element and communicating with said air inlet and said air outlet and through which said air current moves, said passageway communicating with said heater element to draw active vaporized by said heater element into said passageway as said air moves downstream therein.

10. The apparatus of claim 7 wherein said air outlet has a configuration that directs said air current to flow downwardly out of said housing.

11. An apparatus for dispersing a volatile active into air, the apparatus comprising:
a reservoir for containing a composition having a volatile active;
a wick having an emanating surface and communicating with said composition for delivering said composition to said emanating surface;
a heating element in contact with said emanating surface;
a housing substantially enclosing said reservoir, wick and heating element;
a seating flange attached to said reservoir and snap fit into a recess on said housing such that said reservoir is non-rotatably received in said housing, said seating flange enabling proper seating of said of said reservoir in said housing without causing breakage to said reservoir and said heating element;
a source of power communicating with said heating element to heat said heating element and vaporize said volatile active; and
a controller for controlling said source of power to periodically heat said heating element to clean said heating element.

12. The apparatus of claim 11 wherein said controller includes a microprocessor.

13. An apparatus for dispersing a volatile active into air, the apparatus comprising:
a replaceable refill assembly comprising a reservoir for containing a composition having a volatile active and a wick having an emanating surface and communicating with said composition for delivering said composition to said emanating surface;
a retainer for receiving and releasably retaining said replaceable refill assembly;
a heating element engageable with the emanating surface of said wick; and
a spring assembly resiliently supporting said heating element so that when said refill assembly is received by said retainer said spring assembly biases said heating element against said emanating surface and resiliently yields to prevent said heating element from breaking,
wherein said spring assembly comprises a pair of opposing substantially C-shaped spring members, each having a free end and a fixed end, and said heating element comprises a wire extending between said free ends so that the free ends of said spring members move toward each other when said emanating surface engages said heating element.

14. The apparatus of claim 13, further including a pair of connectors for releasably mounting opposite ends of the wire heating element to the free ends of said spring members.

* * * * *